United States Patent
Lenfers et al.

(10) Patent No.: US 6,818,111 B1
(45) Date of Patent: Nov. 16, 2004

(54) MEASUREMENT SENSOR FOR DETERMINING AN OXYGEN CONCENTRATION IN A GAS MIXTURE

(75) Inventors: Martin Lenfers, Aidlingen (DE); Walter Strassner, Schorndorf (DE); Johann Riegel, Bietigheim-Bissingen (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/554,041

(22) PCT Filed: Jul. 9, 1999

(86) PCT No.: PCT/DE99/02124

§ 371 (c)(1),
(2), (4) Date: Oct. 12, 2000

(87) PCT Pub. No.: WO00/14525

PCT Pub. Date: Mar. 16, 2000

(30) Foreign Application Priority Data

Sep. 9, 1998 (DE) .......................................... 198 40 888

(51) Int. Cl.[7] .......................... G01N 27/409; G01N 27/41
(52) U.S. Cl. ........................ 204/425; 204/426; 204/427; 204/406
(58) Field of Search ................................. 204/406, 424, 204/425, 426, 427, 428, 429; 205/783.5, 784, 784.5, 785; 73/23.32

(56) References Cited

U.S. PATENT DOCUMENTS

| | | | | |
|---|---|---|---|---|
| 4,722,779 A | * | 2/1988 | Yamada et al. | 204/410 |
| 5,211,154 A | * | 5/1993 | Brandt | 73/23.32 |
| 6,136,170 A | * | 10/2000 | Inoue et al. | 204/424 |

FOREIGN PATENT DOCUMENTS

| | | |
|---|---|---|
| DE | 44 34 194 | 3/1996 |
| DE | 44 47 033 | 7/1996 |
| DE | 195 16 139 | 11/1996 |
| DE | 198 37 607 | 7/1999 |

OTHER PUBLICATIONS

Diefenderfer, "Principles of Electronic Instrumentation", 2$^{nd}$ ed., pp. 185–190, 1979.*
Diefenderfer, "Principles of Electronic Instrumentation", 2$^{nd}$ ed., p. 14, 1979.*

* cited by examiner

Primary Examiner—Kaj K. Olsen
(74) Attorney, Agent, or Firm—Kenyon & Kenyon

(57) ABSTRACT

A probe is described for determining an oxygen concentration in a gas mixture, in particular in the exhaust gas of internal combustion engines, having a Nernst measuring cell, which has a first electrode (Nernst electrode) which is exposed to the gas mixture to be measured via a diffusion barrier, a second electrode (reference electrode) which is exposed to a reference gas, and a solid electrolyte body arranged between the first and the second electrode, and having a pump cell, which has a first electrode (inner pump electrode) which is exposed to the gas mixture via the diffusion barrier, a second electrode (outer pump electrode) which is exposed to the gas mixture, and a solid electrolyte body arranged between the first and the second electrode. The Nernst electrode and the inner pump electrode are connected at least in some sections via a joint supply conductor to a circuit arrangement for controlling and evaluating the probe. A joint supply conductor resistor of the Nernst electrode and of the inner pump electrode is formed by a loaded voltage divider whose individual resistors are arranged so that the negative feedback of a Nernst voltage circuit and of a pump voltage circuit is optimized, in particular maximized.

6 Claims, 3 Drawing Sheets

MEASUREMENT SENSOR FOR DETERMINING AN OXYGEN CONCENTRATION IN A GAS MIXTURE

FIELD OF THE INVENTION

The present invention relates to a probe for determining an oxygen concentration in a gas mixture, in particular in the exhaust gas of internal combustion engines having the features set forth in the preamble of claim 1.

BACKGROUND INFORMATION

Previously proposed probes determine the oxygen concentration in the exhaust gas of internal combustion engines and are used to influence the setting of the fuel air mixture during operation of the engine. The fuel/air mixture may be in the rich range, i.e., there is an excess of fuel in stoichiometric terms, so that only a small quantity of oxygen relative to other partly unburned components is present in the exhaust gas. In the lean range, in which there is a greater quantity of oxygen relative to the air in the fuel/air mixture, the oxygen concentration in the exhaust gas is correspondingly high. If the fuel/air mixture is of stoichiometric composition, both the amount of fuel and the amount of oxygen in the exhaust gas are reduced.

Lambda sensors which detect a lambda value>1 in the lean range, a lambda value<1 in the rich range, and a lambda value=1 in the stoichiometric range and which are used to determine the oxygen concentration in exhaust gas are known. In this case, the lambda sensor supplies a detection voltage in a known manner, which is conveyed to a circuit arrangement. In known probes, with the help of the circuit arrangement the detection voltage is converted into a pump voltage for a pump cell, which is also a component of the probe and is exposed to the exhaust gas. The pump cell, in which oxygen ions are pumped from an inner pump electrode to an outer pump electrode or vice versa based on the oxygen concentration present. Depending on whether the lambda sensor detects a rich range, i.e., a lambda value<1, or a lean range, i.e., a lambda value>1, the circuit arrangement determines whether the outer pump electrode, which is connected to an active input of the circuit arrangement, is connected as a cathode or as an anode. The inner pump electrode of the pump cell is connected to ground, so that at the pump cell an anodic limit current flows in the case of rich measured gas or a cathodic limit current flows in the case of a lean measured gas. In the case of stoichiometric operation, i.e., if the lambda value=1, the pump voltage is close to 0, so that no limit current flows.

The detection voltage of the probe is determined via a Nernst measuring cell, which determines the difference between the oxygen concentration at a Nernst electrode and that at a reference electrode. The reference electrode is connected to a constant current source, while the Nernst electrode is connected to ground. As a result, the detection voltage is based correspondingly on the difference between the respective oxygen concentrations.

Because the Nernst electrode and the inner pump electrode of the probe are connected to ground, it is known that they can be connected to the circuit arrangement via a joint supply conductor. In this case, the electrodes are initially contacted inside the probe to separate printed conductors, which then come together inside the probe at a contact point to form the joint supply conductor.

By detecting the pump current of the pump cell required to maintain $\lambda=1$ in a measuring space (hollow space) of the probe, it is possible to determine whether the fuel/air mixture used to operate the internal combustion engine is a rich or a lean mixture. If there is a change-over from a rich range to a lean range or vice versa, the pump current drops or increases, respectively. If the engine is being operated in the stoichiometric range, i.e., with a lambda value=1, the pump current has a jump point that marks the transition from the lean range to the rich range and vice versa, respectively.

Referring to FIG. 4, there is seen a conventional connectivity between a gas probe and an operational amplifier. In known probes, it is disadvantageous that because the supply conductor of the Nernst electrode and the inner pump electrode is shared, at least in some sections, their joint supply conductor resistor, which is not only part of the Nernst voltage circuit of the Nernst measuring cell but also part of the pump voltage circuit of the pump cell, causes coupling, which has an impact on lambda=1 ripple. This minimizes the counterswings and overswings in voltage that may occur in the event of a jump response in response to a transition from the rich range to the lean range.

SUMMARY OF THE INVENTION

By contrast, the probe according to the present invention has the advantage that negative feedback of the pump voltage circuit and the Nernst voltage circuit is optimized. Because a joint supply conductor resistor of the Nernst electrode and of the inner pump electrode is formed by a loaded voltage divider whose individual resistors are arranged so that negative feedback of a Nernst voltage circuit and of a pump voltage circuit is increased, the lambda=1 ripple can be reduced. The individual resistors are arranged so that when the detection voltage of the Nernst measuring cell transitions from the lean range to the rich range or vice versa, this produces a result via the jump point that triggers an anodic or cathodic limit current, respectively, via the pump cell, so that negative feedback via the joint supply conductor section of the Nernst measuring cell and the pump cell can be achieved.

According to a preferred embodiment of the present invention, an additional external resistor is connected in series to the joint supply conductor section of the Nernst measuring cell and the pump cell. Thanks to this additional external resistor, the total resistance of the joint supply conductor section is increased, so that at the constant current at which the Nernst measuring cell is operated the detection voltage is greater, so that the influence of negative feedback is increased by the cathodic or alternatively anodic limit current, which also flows through the additional resistor.

According to a further preferred embodiment of the present invention, a cross section of the joint supply conductor section is reduced. Reducing the cross section is another way to increase the resistance value of the joint supply conductor section, so that this is also a straightforward way of increasing negative feedback between the Nernst voltage circuit and the pump voltage circuit.

According to a further preferred embodiment of the present invention, the contact point where the printed conductor of the inner pump electrode meets the printed conductor of the Nernst electrode is moved spatially as close as possible to the electrodes, so that the length of the joint supply conductor section increases, so that the resistance of this joint supply conductor section is also increased by a defined amount.

DESCRIPTION OF THE EXEMPLARY EMBODIMENTS

Figure 1:
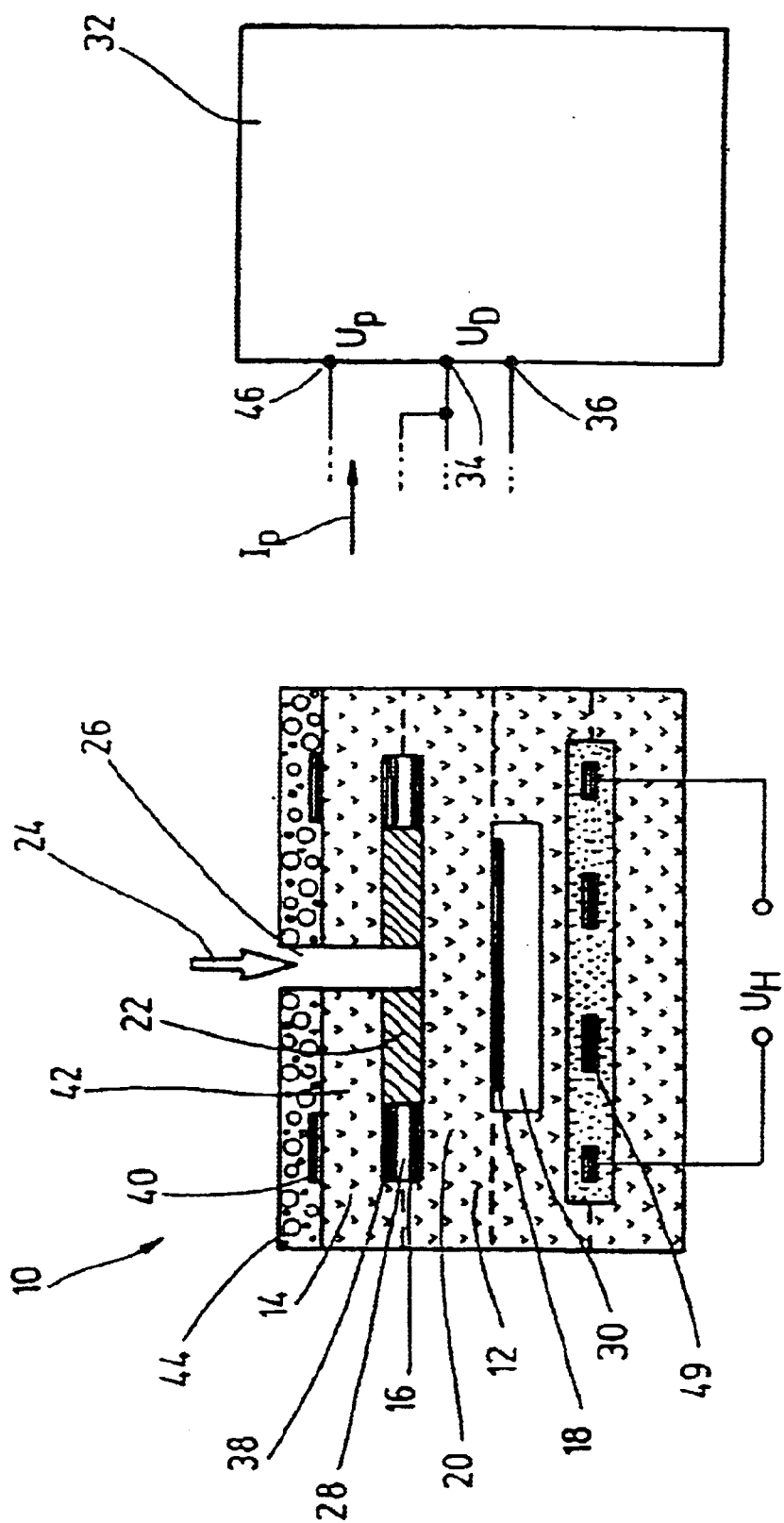
FIG. 1 shows a section through the head of a probe.

FIG. 1 shows a section through a measuring head of a probe 10. Probe 10 is designed as a planar broadband probe and includes a plurality of individual layers which are arranged one above the other and may, for example, be structured via film casting, punching, screen printing, lamination, cutting, vitrification or other processes. The processes used to achieve layer structure will not be discussed in greater detail in the context of the present description, as this is known.

Probe 10 is used to determine an oxygen concentration in the exhaust gas of internal combustion engines, so as to generate a control signal for setting a fuel/air mixture used to operate the internal combustion engine. Probe 10 has a Nernst measuring cell 12 and a pump cell 14. Nernst measuring cell 12 has a first electrode 16 (Nernst electrode) and a second electrode 18 (reference electrode), between which a solid electrolyte 20 is arranged. Electrode 16 is exposed to exhaust gas 24 to be measured via a diffusion barrier 22. Probe 10 has a measuring opening 26 to which exhaust gas 24 can be supplied. Diffusion barrier 22 extends at the base of measuring opening 26, a hollow space 28 being formed within which electrode 16 is arranged. Electrode 18 of Nernst measuring cell 12 is arranged in a reference air channel 30 and exposed to a reference gas, e.g., air, present in reference air channel 30. Solid electrolyte 20 is made of, for example, yttrium-oxide-stabilized zirconium oxide, while electrodes 16 and 18 are made of, for example, platinum.

Probe 10 is connected to a circuit arrangement 32 (only indicated here) which evaluates the signals of probe 10 and controls the probe. Electrodes 16 and 18 are connected to inputs 34 and 36, respectively, of circuit arrangement 32, to which detection voltage $U_D$ of Nernst measuring cell 12 is applied.

Pump cell 14 includes a first electrode 38 (inner pump electrode) and a second electrode 40 (outer pump electrode) between which a solid electrolyte 42 is arranged. Solid electrolyte 42 is in turn made of, for example, a yttrium-oxide-stabilized zirconium oxide, while electrodes 38 and 40 may in turn be made of platinum. Electrode 38 is also arranged in hollow space 28 and is thus also exposed to exhaust gas 24 via diffusion barrier 22. Electrode 40 is covered by a protective layer 44, which is porous, so that electrode 40 is directly exposed to exhaust gas 24. Electrode 40 is connected to an input 46 of circuit arrangement 32, while electrode 38 is connected to electrode 16 and, along with it, is connected jointly to input 34 of circuit arrangement 32. This joint supply conductor of electrodes 16 and 38 connected to circuit arrangement 32 will be discussed in greater detail below with reference to FIGS. 2 and 3.

Probe 10 also includes a heating device 49 which is formed by a meandering heating element and to which a heating voltage $U_H$ can be applied.

Probe 10 functions as follows:

Exhaust gas 24 enters hollow space 28 via measuring opening 26 and diffusion barrier 22 and is thus present at electrode 16 of Nernst measuring cell 12 and electrode 38 of pump cell 14. A difference in the oxygen concentration at electrode 16 and that at electrode 18, which is exposed to the reference gas, arises based on the oxygen concentration in the exhaust gas to be measured. Electrode 16 is connected to a current source of circuit arrangement 32, which supplies a constant current, via terminal 34. A specific detection voltage $U_D$ (Nernst voltage) arises based on a difference between the oxygen concentration present at electrode 16 and that at electrode 18. Here, Nernst measuring cell 12 functions as a lambda sensor that detects whether a high oxygen concentration or a low oxygen concentration is present in exhaust gas 24. It is clear from the oxygen concentration whether the fuel/air mixture used to operate the internal combustion engine is a rich or a lean mixture. If there is a change-over from the rich range to the lean range or vice versa, detection voltage $U_D$ drops or increases, respectively. With stoichiometric operation, i.e., with a lambda value=1, detection voltage $U_D$ has a jump point that marks the transition from a lean range to a rich range or vice versa, respectively.

With the help of circuit arrangement 32, detection voltage $U_D$ is used to determine pump voltage $U_P$, which is applied to pump cell 14 between its electrodes 38 and 40, respectively. Pump voltage $U_P$ is negative or positive based on whether detection voltage $U_D$ signals that the fuel/air mixture is in the rich or lean range, so that electrode 40 is connected either as a cathode or as an anode. Accordingly, a pump current $I_P$ is established and can be measured via a measuring device of circuit arrangement 32. With the help of pump current $I_P$, oxygen ions are pumped from electrode 40 to electrode 38 or vice versa. Measured pump current $I_P$ is used to control a device for setting the fuel/air mixture used to operate the internal combustion engine.

Figure 2:
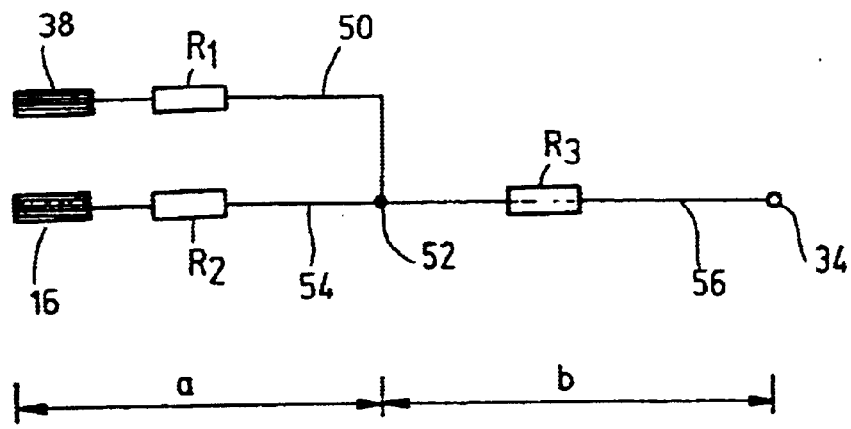
FIG. 2 shows an equivalent circuit diagram of a joint supply conductor of a Nernst electrode and an inner pump electrode of the probe.

The detection voltage circuit (Nernst voltage circuit) and the pump voltage circuit are coupled to circuit arrangement 32 via the joint supply conductor of electrodes 16 and 38, respectively. In FIG. 2, an equivalent circuit diagram illustrating how electrodes 16 and 38 are connected to circuit arrangement 32 is shown. It is clear from the equivalent circuit diagram that electrode 38 is initially connected to a contact point 52 via a printed conductor section 50. Electrode 16 is also connected to contact point 52 via a printed conductor section 54. A printed conductor section 56 connects contact point 52 to input 34 of circuit arrangement 32. Contact point 52 is arranged inside probe 10 and is located at a geometric distance a from electrodes 16 and 38, respectively, indicated here. A geometric distance b for joint supply conductor section 56 of electrodes 16 and 38 results, corresponding to section a.

Conductor section 50 has an internal resistor R1, conductor section 54 has an internal resistor R2, and conductor section 54 has an internal resistor R3. Resistors R1, R1, and R3 form a loaded voltage divider, the constant current applied to Nernst measuring cell 12 flowing via conductor sections 54 and 56, while pump current $I_P$ flows via conductor sections 50 and 56.

Figure 3A:
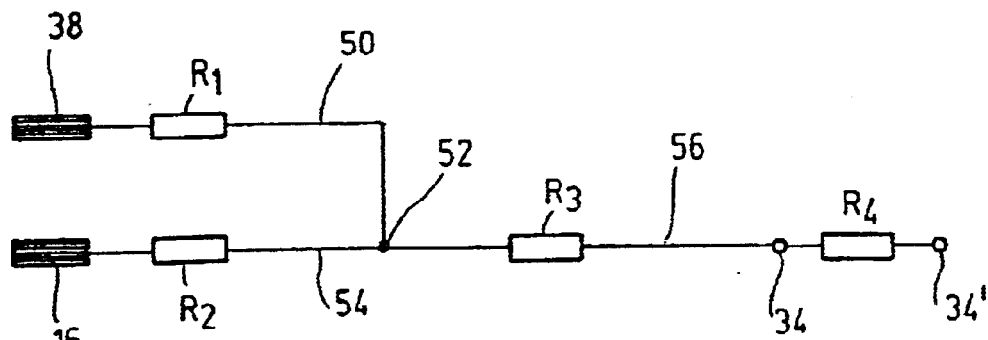
FIG. 3a shows one embodiment for influencing the resistances of the joint supply conductor according to FIG. 2.

FIG. 3a shows a first embodiment variant for arranging the loaded voltage divider formed by resistors R1, R2, and R3. An additional resistor R4 is connected between terminal 34 and circuit arrangement 32 (FIG. 1). This effectively increases the resistance value of joint supply conductor section 56 of electrodes 16 and 38, the resistance being the sum of resistances R3 and R4. Thanks to this greater resistance R3+R4, the Nernst voltage increases given the constant current applied to Nernst measuring cell 12 via circuit arrangement 32.

Figure 3B:
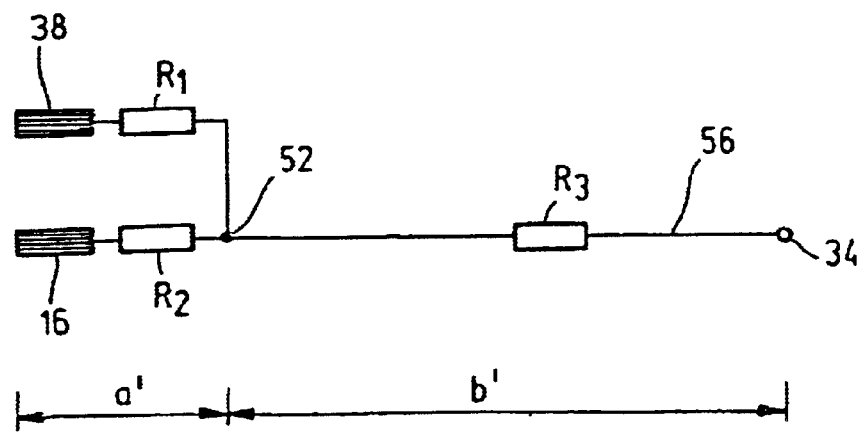
FIG. 3b shows a second embodiment for influencing the resistances of the joint supply conductor according to FIG. 2.
Figure 4:
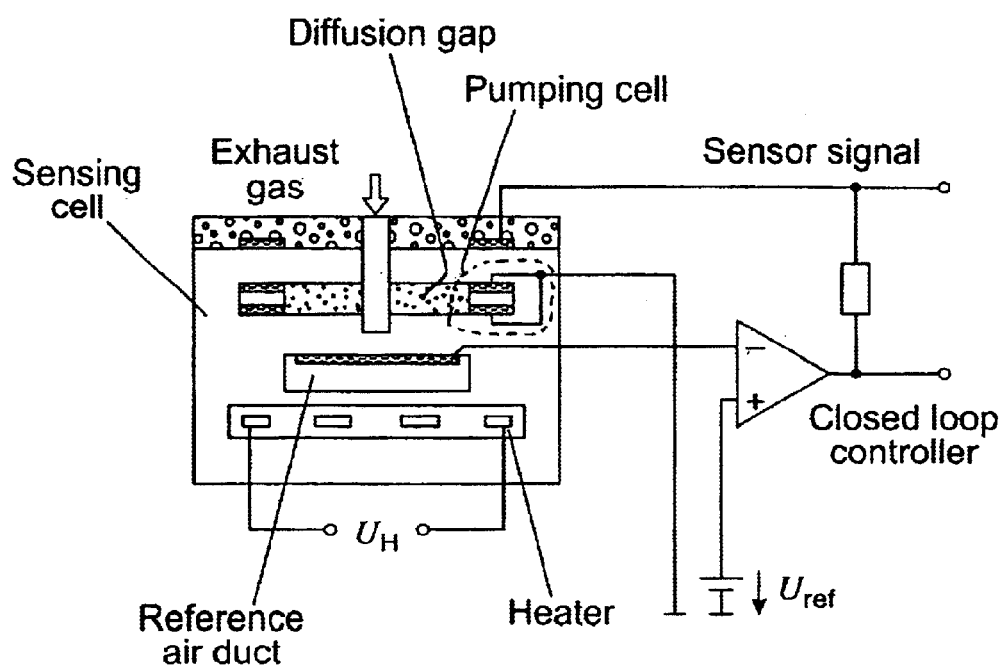
FIG. 4 shows connectivity between a gas probe and an operational amplifier.

According to the embodiment variant shown in FIG. 3b, contact point 52 is moved geometrically closer to electrodes 16 and 38, so that the length of joint supply conductor section 56, i.e., distance b' between contact point 52 and terminal 34, is increased. As a result, the resistance value of resistor R3 is increased relative to the initial embodiment shown in FIG. 2. In particular, this causes supply conductor resistor R3 to have a positive temperature coefficient.

According to a further embodiment variant (not shown), joint supply conductor section 56 between contact point 52 and terminal 34 may have a smaller cross section than that of sections 50 and 54, respectively, so that as a result the resistance value of resistor R3 increases.

What is claimed is:

1. A probe for determining an oxygen concentration in a gas mixture, comprising:
   a Nernst measuring cell including:
      a Nernst electrode exposed to the gas mixture to be measured via a diffusion barrier, a reference electrode exposed to a reference gas, and a solid electrolyte body arranged between the Nernst electrode and the reference electrode;
   a pump cell including:
      an inner pump electrode exposed to the gas mixture via the diffusion barrier, an outer pump electrode exposed to the gas mixture, and a solid electrolyte body arranged between the inner pump electrode and the outer pump electrode;
   a joint supply conductor section through which the Nernst electrode and the inner pump electrode are connected to a circuit arrangement for controlling and evaluating the probe; and
   a loaded voltage divider including a plurality of resistors that are arranged such that a negative feedback of a Nernst voltage circuit and of a pump voltage circuit is optimized, the plurality of resistors including a joint supply conductor resistor associated with the Nernst electrode and the inner pump electrode;
   wherein magnitudes of the plurality of resistors are chosen so as to reduce a rippling effect at a stoichiometric point.

2. The probe according to claim 1, wherein:
   the gas mixture corresponds to an exhaust gas of an internal combustion engine.

3. The probe according to claim 1, further comprising:
   an additional external resistor connected in series to the joint supply conductor section.

4. The probe according to claim 1, wherein:
   a cross section of the joint supply conductor section is minimized.

5. The probe according to claim 1, further comprising:
   printed conductor sections via which the Nernst electrode and the inner pump electrode are connected to a contact point, wherein:
   the cross section of the joint supply conductor section is smaller than a cross section of the printed conductor sections.

6. The probe according to claim 1, wherein:
   the Nernst electrode and the inner pump electrode are connected to the circuit arrangement via the joint supply conductor section by a contact point, and
   the contact point is located directly downstream of the Nernst electrode and the inner pump electrode at a first distance such that a second distance of the joint supply conductor section is of a maximum length.

* * * * *

UNITED STATES PATENT AND TRADEMARK OFFICE
CERTIFICATE OF CORRECTION

PATENT NO. : 6,818,111 B1
DATED : November 16, 2004
INVENTOR(S) : Martin Lenfers et al.

It is certified that error appears in the above-identified patent and that said Letters Patent is hereby corrected as shown below:

Column 2,
Line 3, change "a change-over" to -- a changeover --

Column 3,
Lines 15-16, change "Description of the Exemplary Embodiments" to -- Detailed Description --

Signed and Sealed this

Twelfth Day of July, 2005

JON W. DUDAS
*Director of the United States Patent and Trademark Office*